US011683650B2

(12) United States Patent
Troelsen et al.

(10) Patent No.: US 11,683,650 B2
(45) Date of Patent: *Jun. 20, 2023

(54) ANTENNA CONFIGURATION FOR A HEARING AID SYSTEM

(71) Applicant: Oticon Medical A/S, Smørum (DK)

(72) Inventors: Jens Troelsen, Smørum (DK); Oleksandr Rybalko, Smørum (DK)

(73) Assignee: Oticon Medical A/S, Smørum (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/701,140

(22) Filed: Mar. 22, 2022

(65) Prior Publication Data

US 2022/0217482 A1      Jul. 7, 2022

Related U.S. Application Data

(63) Continuation of application No. 16/868,124, filed on May 6, 2020, now Pat. No. 11,310,610.

(30) Foreign Application Priority Data

May 7, 2019   (EP) .................................. 19172889

(51) Int. Cl.
   *H04R 25/00*   (2006.01)

(52) U.S. Cl.
   CPC ......... *H04R 25/554* (2013.01); *H04R 25/606* (2013.01)

(58) Field of Classification Search
   CPC ........................... H04R 25/554; H04R 25/606
   USPC .......................................................... 381/315
   See application file for complete search history.

(56) References Cited

U.S. PATENT DOCUMENTS

2018/0108994 A1     4/2018   Lee

FOREIGN PATENT DOCUMENTS

| EP | 3 404 933 A1 | 11/2018 |
| EP | 3736906 A1 | 11/2020 |
| WO | WO 2010/056770 A1 | 5/2010 |

*Primary Examiner* — Phylesha Dabney
(74) *Attorney, Agent, or Firm* — Birch, Stewart, Kolasch & Birch, LLP

(57) ABSTRACT

A hearing aid system includes an implant unit and a sound processor unit. The implant unit may be a transcutaneous bone anchoring stimulator configured to provide an acoustical vibration to the skull of the user wearing the hearing aid system. The implant unit may be cochlear stimulator configured to stimulate neural nerves of the cochlear of the user wearing the hearing aid system. The sound processor unit may be a housing attached to the skin of the user and attached to the implant unit by a magnetic force.

20 Claims, 6 Drawing Sheets

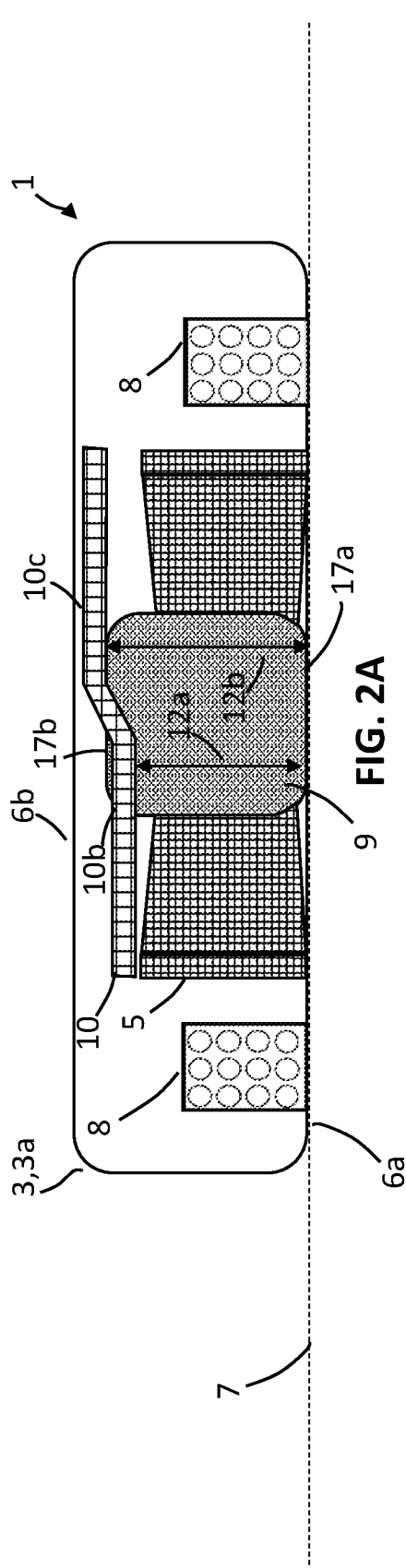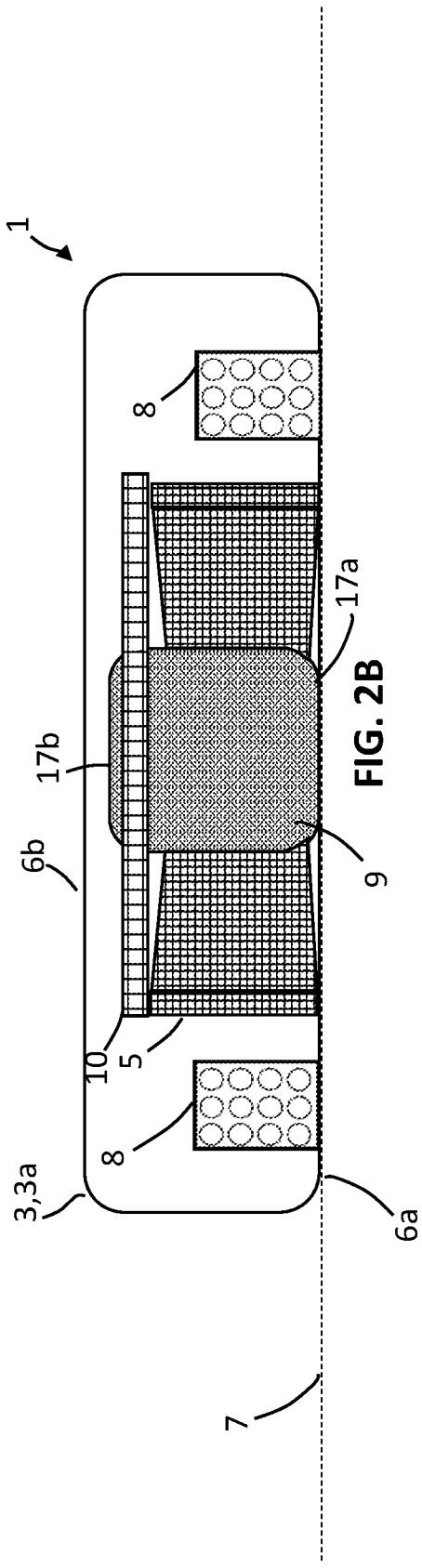

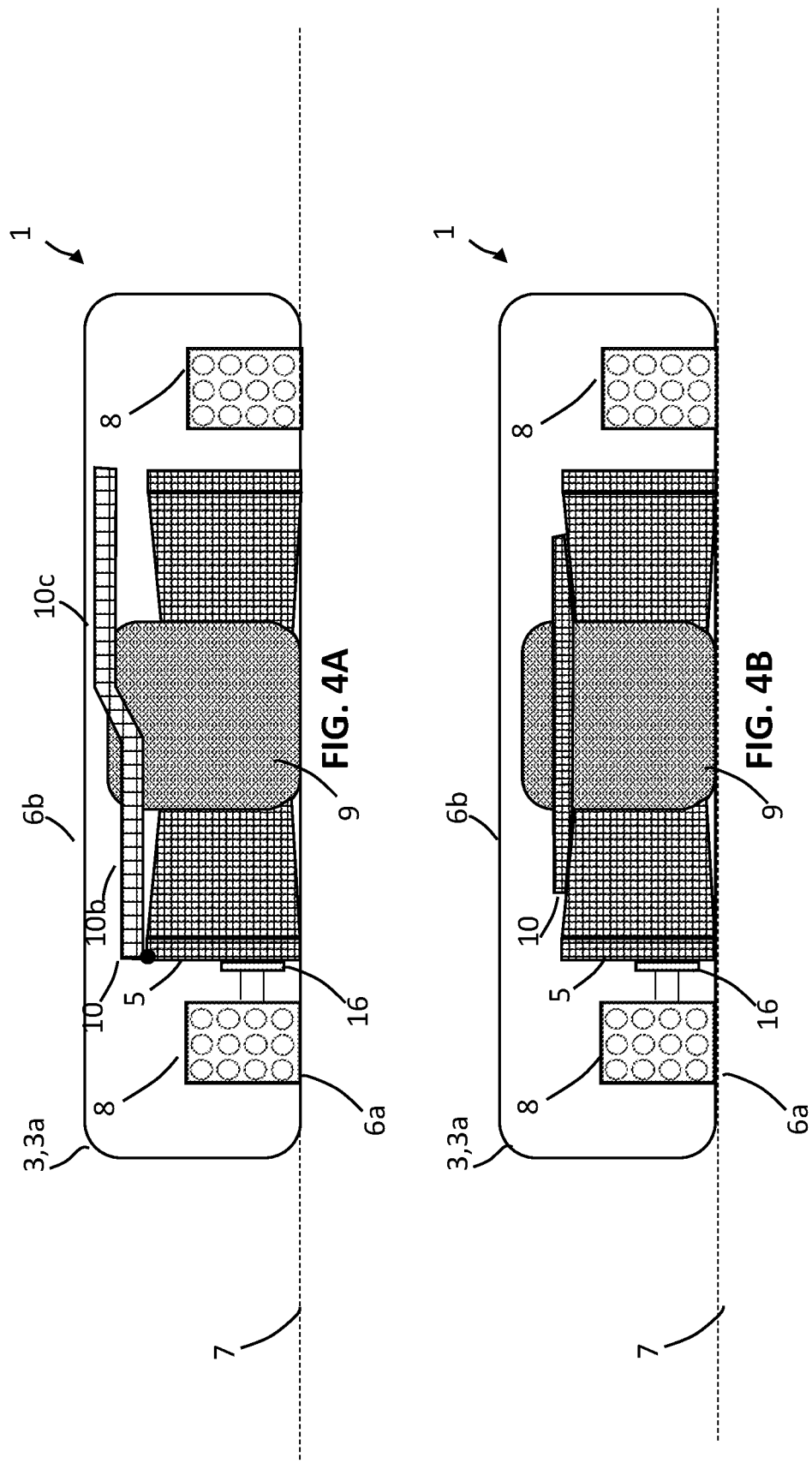

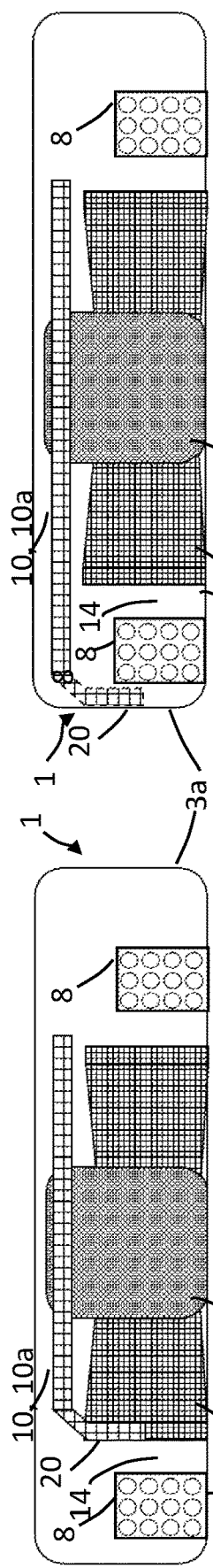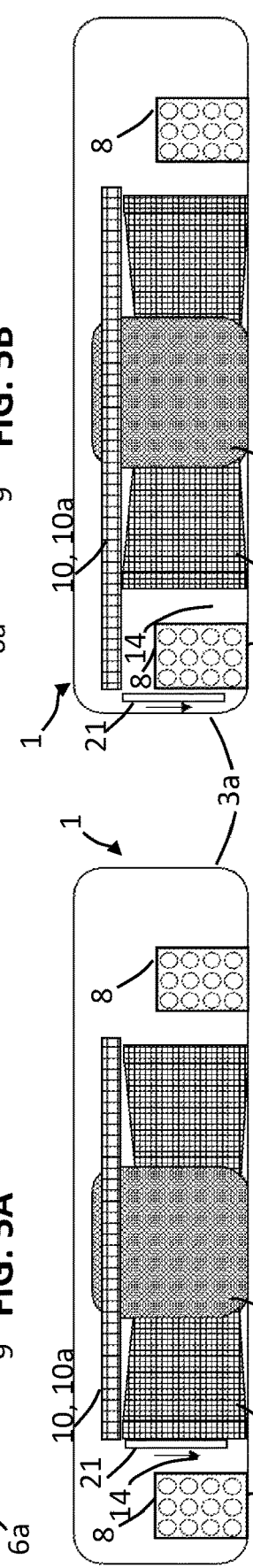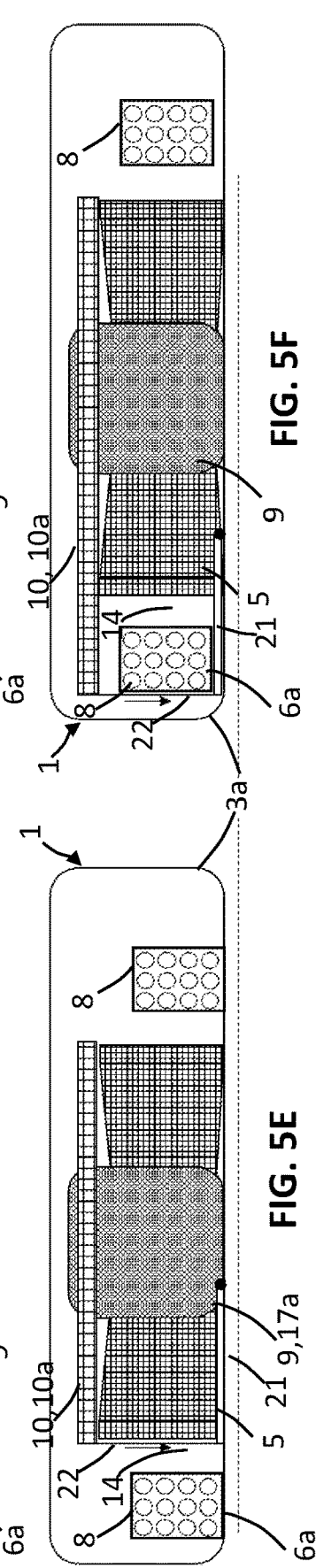

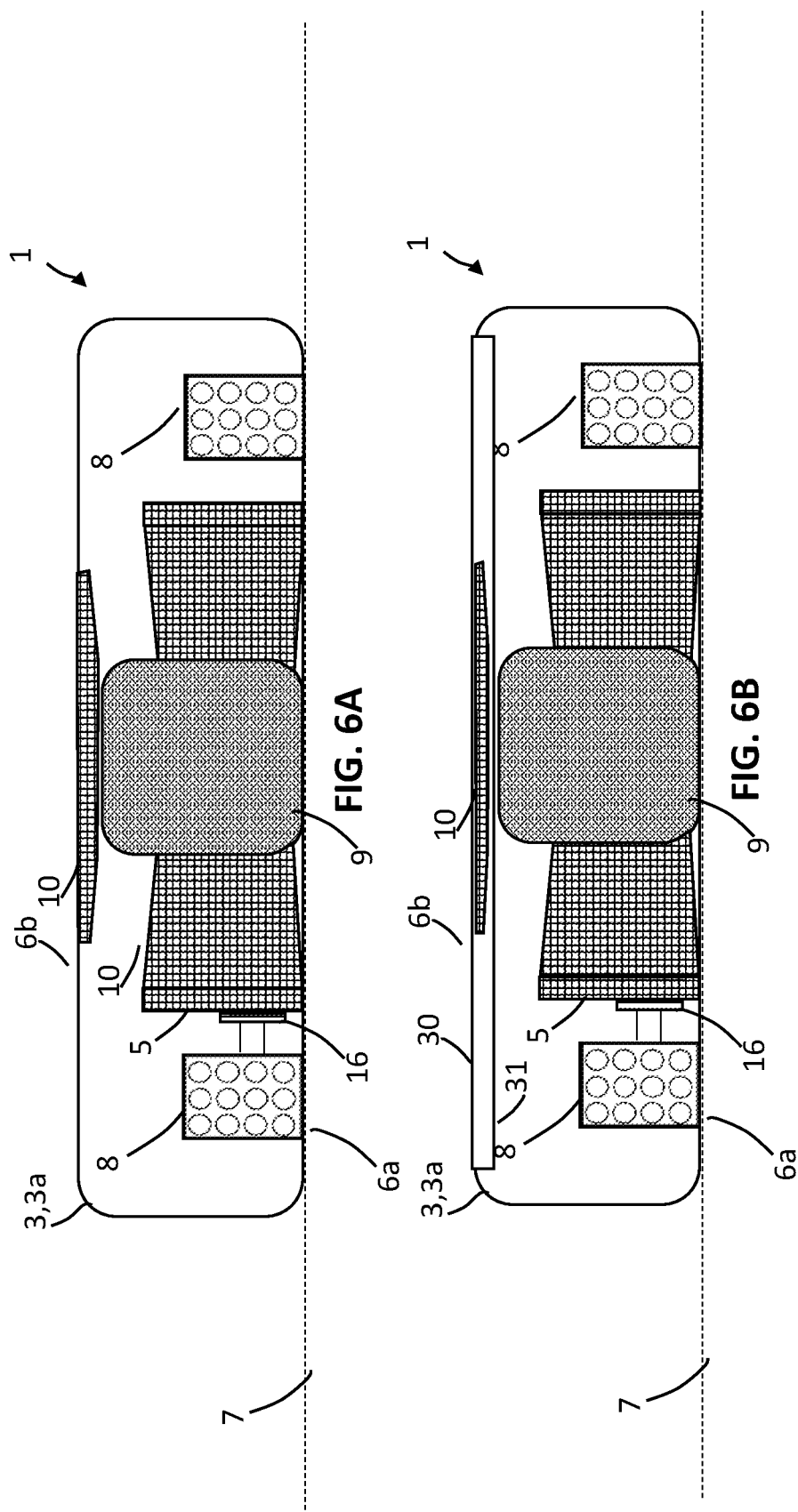

ANTENNA CONFIGURATION FOR A HEARING AID SYSTEM

This application is a Continuation of copending application Ser. No. 16/868,124, filed on May 6, 2020, which claims priority under 35 U.S.C. § 119(a) to Application No. 19172889.8, filed in Europe on May 7, 2019, all of which are hereby expressly incorporated by reference into the present application.

TECHNICAL FIELD

The present disclosure relates to hearing aids. More particularly, the disclosure relates to an antenna configuration of a hearing aid system.

BACKGROUND

Hearing aids for compensating a wearer's hearing loss are well known. Hearing aids are very dense applications and when integrating wireless applications, it may sometimes be difficult to find sufficient space for required or desired antenna components, and to arrange an antenna within a space where radiation of unwanted electromagnetic noise is minimized or reduced. Furthermore, the needs of a user of a hearing aid becomes more demanding as the technology is in a constant development. The constant developing of the demands of the user results in higher expectation of the performance of the hearing aid, such as better radiation efficiency of the antenna, improved bandwidth of the antenna, better electromagnetic coupling between the hearing aid and an external device being placed in a pocket of the user. The external device could for example a smartphone, a mobile phone, a tablet, a pocket computer etc.

The hearing aids are very dense applications, and which puts high demands to the size constraints, and therefore, it is not possible to implement multiple components into the hearing aid that would result in a hearing aid which fulfils the demands mentioned above.

The problem to be solved is to provide an antenna configuration which fulfils one or more of the demands mentioned above. The present disclosure provides at least an alternative to the prior art.

SUMMARY

An object of the disclosed invention is to provide a hearing aid system with improved antenna performance and to provide a compact hearing aid system. The hearing aid system comprising an implant unit and a sound processor unit. The implant unit may be a transcutaneous bone anchoring stimulator configured to provide an acoustical vibration to the skull of the user wearing the hearing aid system. The implant unit may be cochlear stimulator configured to stimulate neural nerves of the cochlear of the user wearing the hearing aid system. The sound processor unit may be a housing attached to the skin of the user and attached to the implant unit by a magnetic force. Thus, the sound processor may include two parts, a first part being attached to the implant unit by the magnetic force and the second part is arranged behind an ear of the user wearing the hearing aid system. The first part and the second part may be connected by a connecting member. The second part may be denoted as a behind-the-ear hearing aid which is known to be arranged on and behind the ear.

The implant unit may be arranged on to the skull of the user by screws or any kind of fixture means.

The sound processor unit may comprise a housing including a first surface facing towards a skin of a user and at least a second surface facing away from the skin of the user, and wherein the housing comprising an electrical circuitry configured to receive and process an audio signal and to provide a processed audio signal.

The audio signal may be received by an antenna comprised by the housing or by a microphone which is comprised by the housing. The electrical circuitry may include electrical components and passive components, wherein the electrical components may be a selection of one or more components of a group comprising one or more microphones, micro wave power amplifiers, clock circuits, voltage-controlled oscillators, analog-to-digital/digital-to-analog converters, memories etc. The passive components may be a selection of one or more components of a group comprising one or more resistances, capacitors, coils, components which only are configured to dissipate, store and/or release power.

The housing of the sound processor unit may include a coil unit configured to transfer the processed audio signal to the implant unit.

The coil unit may be arranged in vicinity of the first surface, wherein the first surface is arranged on to the skin of the user wearing the hearing aid system. Ideally, the coil unit is arranged as close as possible to the skin of the user for achieving as high as possible coupling efficiency through the skin and tissue of the user and to the implant unit.

The coil unit may be furthermore configured to transfer data signal which is processed by the electrical circuitry. The data signal may be generated by the electrical circuitry based on a command or a signal received by an antenna comprised by the housing.

The housing of the sound processor unit may include a magnet configured to align the sound processor unit to the implant unit. The magnet may be arranged within a magnet housing comprised by the housing.

The housing of the sound processor unit may include an antenna including a radiating part configured to radiate an electromagnetic field for receiving the audio signal and/or the data signal, and wherein the antenna includes an aperture, wherein the aperture may be configured to receive at least a part of the magnet, and wherein the antenna is arranged between the coil unit and the second surface.

The radiating part may be a conductive track made of copper or any kind of conductive material formed on a printed circuit board or a flex print. The radiating part is the active part of the antenna which is being fed with a current via a galvanic coupling to a feeding point. A passive part, such as a parasitic element may be fed via an inductive or a capacitive coupling to the active part, i.e. the radiating part.

To obtain a more compact sound processor unit, the aperture of the antenna has the advantage of reducing the space needed for the antenna within the housing. If the antenna was arranged on top of the magnet then the antenna and the housing must adapt to one and other. The adaptation to each other may result in a larger housing, a shaping of the housing which is less ergonomic suitable for the user and/or the performance of the antenna may be affected negatively.

Thus, the antenna may be arranged such that the aperture receives the complete magnet or at least a part of the magnet. The advantage is an improved compactness of the sound processor unit when comparing to the situation where the aperture is receiving only a part of the magnet. Furthermore, the antenna becomes easier to arrange within the housing because the distance between the antenna and the first surface or the second surface of the housing can be adjusted freely.

The coil unit may include multiple coils.

The radiating part may be arranged circumferential to the aperture having a first end connected to a feeding point and a second end connected to a ground plane. The radiating part may be formed by a conductive path formed on a substrate, and wherein the substrate includes the aperture. The conductive path may for example be made of cobber or other kind of conductive material. When the radiating part is arranged circumferential to the aperture then the radiating part achieves a radiation characteristic which is like a loop antenna. The radiating part may be characterized as a loop antenna. The advantage of the radiation characteristic being like a loop antenna is that an electric field is generated by the antenna which is perpendicular or at least partly perpendicular to the skin of the user when the hearing aid system is worn by the user. The effect of the electric field being perpendicular to the skin of the user is that the electromagnetic waves generated by the antenna is more suitable to travel along the body of the user and which provides a better coupling between the antenna and an antenna of an external device, such as a smartphone, placed in vicinity to the body of the user.

The perpendicular electric field is relevant for one purpose, which is for providing electromagnetic waves which may by suitable for travel along the body of the user. In this case, the perpendicular electric field is relevant for establishing communication between a first sound processor unit and a second sound processor unit via the antenna of both sound processor units. The first sound processor unit is arranged on the left ear of the user and the second sound processor unit is arranged on the right ear of the user. In this case the hearing aid system is a binaural hearing aid system. In other cases, it may not be an advantage to have the perpendicular electric field, for example, when the user is wearing only one sound processor unit, and thereby, it would not be necessary to have the perpendicular electric field. Instead, you may want a better connection between the antenna and an antenna of a smartphone placed in a pocket of the user. In this example, the antenna of the sound processor unit will preferably have the electromagnetic field directed downwards.

Thereby, the shape of the antenna provides an improved coupling efficiency to an antenna of external device which is placed close to the body of the user of the hearing aid system.

The coil unit may be connected to a decoupler configured to decouple the coil unit at an operating frequency of the antenna. The decoupler may be an inductance or an integrated circuit (IC) having a resonance frequency at the operating frequency of the antenna.

By decoupling the coil unit an improved radiation efficiency or coupling efficiency of the antenna is obtained, and especially, the coupling to the antenna of the external device is significantly improved.

The performance of the antenna is strongly depended on how the coil unit is arranged within the hearing aid system, it is seen by a large performance variation of the antenna from product to product, i.e. a hearing aid system. Then, by applying the decoupling of the coil unit to the hearing aid system a smaller performance variation of the antenna from product to product is seen. That means, the performance of the antenna has become less sensitive to the performance and placement of the coil unit.

Furthermore, by decoupling the coil units also decrease the risk of noise coming from the KHz system will reach the BLE antenna and reduce the BLE sensitivity.

The antenna may be arranged such that the magnet is arranged within the aperture. By doing this, the size of the housing is reduced even more when comparing to the example where at least a part of the magnet is arranged within the aperture.

The connections of the radiating part to the feeding point and the ground plane may be arranged on a first side of the magnet, and the connection of the coil unit to the decoupler may be arranged on a second side of the magnet, wherein the first side of the magnet is opposite to the second side of the magnet. In this example, the magnet is acting as a shield between the feeding point and the connection point to the decoupler, and between the ground point and the connection point to the decoupler.

The connections of the radiating part to the feeding point and the ground plane may be arranged on the same side of the magnet as where the connection to the decoupler is arranged.

An operating frequency of the antenna may be within a frequency range of 2.4 GHz to 6 GHz. An operating frequency of the coil unit may be within a frequency range from 10 KHz to 150 KHz or about 60 KHz or about 120 KHz.

The magnet includes a first end surface arranged in vicinity to the second surface of the housing and a second end surface arranged in vicinity to the first surface of the housing, and wherein a first part of the radiating part of the antenna may arranged between the first end surface and the second surface of the housing. Thereby, the magnet does not provide any shield of the first part of the radiating part. This provides an improved "visibility" of the antenna in any directions. That means the antenna radiation efficiency has improved.

The antenna may soldered, glued, or preferably with a conductive adhesive. The antenna may be wired connected to the electronic circuit. The antenna may be part of the electrical circuit, i.e. the antenna may be formed or cast into the electrical circuit.

The housing has a longitudinal axis along a first length of the sound processor unit, and the sound processor unit has a transverse axis along a second length of the sound processor. The longitudinal axis is perpendicular to the transvers axis, and the first length is longer than the second length.

The antenna may include another radiating part extending towards the first surface of the housing, and wherein the another radiating part is connected to the radiating part.

The another part may be bended and extended along or partly along a transverse axis of the sound processor unit. The another part may extend towards the first surface of the housing.

The purpose of having the another part extending towards the first surface is for improving the amount of electric field going towards the skin of the user, and thereby, improving the radiation efficiency of the antenna towards an antenna of an external device, such as a smartphone, placed in vicinity to the body of the user, e.g. in a pocket of a pants of the user.

The another radiating part may extend towards the first surface of the housing within or outside an area which is circumference by the coil unit. When it is outside the area circumference by the coil unit the another radiating part is less disturbed by the magnetic field generated by the coil unit. Thereby, an improved performance of the antenna is obtained in view of the other example where the another radiating part is extending towards the first surface of the housing within the area which is circumference by the coil unit.

Thus, the advantage of extending the another radiating part towards the first surface of the housing within the area is that the size of the housing can be reduced in view of the example where the another radiating part is extending towards the first surface of the housing outside the area which is circumference by the coil unit.

The antenna may include a passive resonant element being connected capacitively to the radiating part of the antenna, and wherein the passive resonant element may be arranged between the first surface of the housing and the radiating part of the antenna The passive resonant element may be arranged such that it extends along the transverse axis of the housing and towards the first surface. The passive resonant element may be part of the electrical circuitry.

The purpose of having the passive resonant element extending towards the first surface is for improving the amount of electric field going towards the skin of the user, and thereby, improving the radiation efficiency of the antenna towards an antenna of an external device, such as a smartphone, placed in vicinity to the body of the user, e.g. in a pocket of a pants of the user.

The antenna may include a passive resonant element being connected galvanic to the radiating part of the antenna via a connecting element, wherein the connecting element is arranged between the first surface of the housing and the radiating part of the antenna.

The passive resonant element may be arranged in parallel or partly in parallel with the first surface.

By applying both the another radiating part and the passive resonant element the amount of electric field going towards the skin of the user is even more improved. The another radiating part may be connected to the radiating part at one end of the radiating part and the passive resonant element may be connected to the radiating at another end of the radiating part.

The electric field going towards the skin of the user may be substantially perpendicular to the skin of the user.

The passive resonant element may be connected to a ground for enhancing the electric field going towards the skin of the user.

The passive resonant element may arranged within a near field of the electrical circuitry, and the passive resonant element being connected to a ground through energy dissolving means to terminate and dissolve electromagnetic radiation noise from at least at part of an area of the electrical circuit and/or other electrical components within the housing.

Thereby, the performance is even more improved in respect to radiation efficiency. Thus, combining the approach of connecting the coil unit to the decoupler and connecting the radiating part to the passive resonant element, then the risk of unwanted noise to interfere with the antenna is even more reduced. Thereby, the performance of the antenna is even more improved.

The aperture may be configured to receive at least the magnet, and wherein the antenna may be arranged between the coil unit and the second surface.

The aperture may be configured to receive at least a battery and/or the magnet.

The passive resonant element may be implemented as a notch filter filtering the electromagnetic radiation noise.

A hearing aid system may comprise a fixture mean configured to be arranged in a skull of a user and a sound processor unit configured to be attach to the fixture mean. The system may further comprise a housing including a first surface configure to be facing towards a skin of a user and at least a second surface configured to be facing away from the skin of the user. The aperture of the antenna may not receive the complete magnet or a part of the magnet, and the antenna is arranged between the second surface and the coil unit. The advantage is an improved connection between the antenna and an external antenna of a mobile device, such as a smartphone or any accessories comprising an antenna, because the antenna is not shadowed by for example the magnet and/or the coil unit. In yet another example the antenna may be formed or arranged in the second surface of the housing of the sound processor unit, or in between an inner surface of the housing and an outer surface of the housing, wherein the inner surface and the outer surface face away from the skin of the user when the user is wearing the sound processor unit. In one example, the aperture is then configured to receive a cap which is configured to be attached and/or detached to the second surface of the sound processor unit, and when removing the cap, the user is able to take out the magnet through the second surface and through the aperture of the antenna, and thereby, the aperture of the antenna is configured to receive the complete magnet or at least a part of the magnet when removing the magnet away from the sound processor unit.

The housing may comprise an electrical circuitry configured to receive and process an audio signal and to provide a processed audio signal, a transducer including a coil, a magnet and a mass unit, and where the transducer is configured to apply a vibration onto to the fixture mean. The system may further comprise an antenna including a radiating part configured to radiate an electromagnetic field perpendicular or at least partly perpendicular to the skin of the user for receiving the audio signal and/or a data signal, and wherein the antenna includes an aperture, and the aperture is configured to receive at least a part of the transducer.

BRIEF DESCRIPTION OF DRAWINGS

The objects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each object may each be combined with any or all features of the other objects. These and other objects, features and/or technical effect will be apparent from and elucidated with reference to the illustrations described hereinafter in which:

FIGS. 2A and 2B illustrate two examples of a hearing aid system where an antenna is arranged differently within a housing of a hearing aid system;

FIGS. 4A and 4B illustrate two examples of a hearing aid system where a coil is connected to a decoupler;

FIGS. 5A to 5F illustrate different examples of a hearing aid system where the antenna is configured differently; and FIGS. 6A and 6B illustrate different examples of a hearing aid system where the antenna is configured differently.

DETAILED DESCRIPTION

Figure 1B:
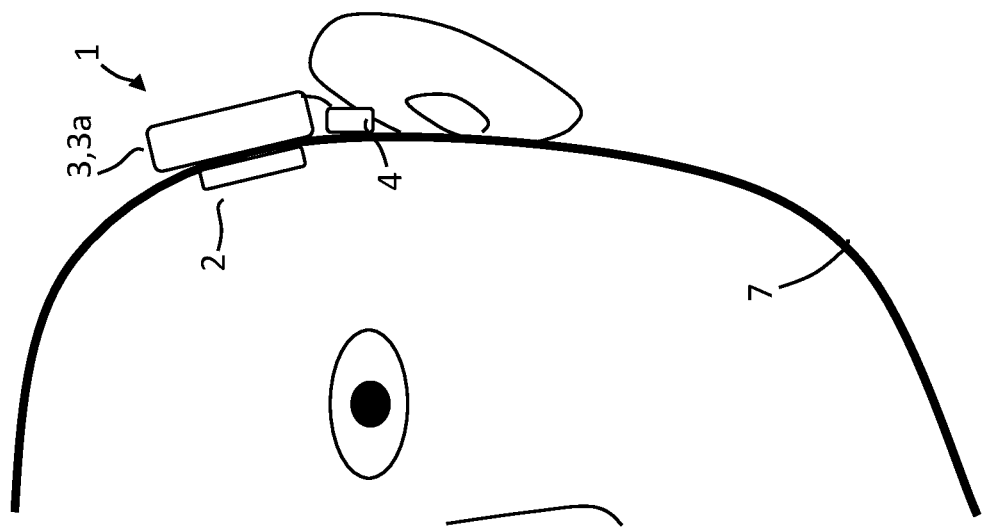
FIGS. 1A and 1B illustrate two examples of a hearing aid system being worn by a user

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device, such as the implant unit and/or the sound processor, may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals may be provided in the form of an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

The hearing aid system refers to a system comprising one or two hearing devices, and a "binaural hearing system" refers to a system comprising two hearing devices where the devices are adapted to cooperatively provide audible signals to both of the user's ears. The hearing aid system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a Smartphone or other electronic device, the Smartphone/electronic device possibly running an application that controls functionality of the at least one hearing device.

In general, a hearing device, such as an implant unit and/or a sound processor unit includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

Figure 1A:
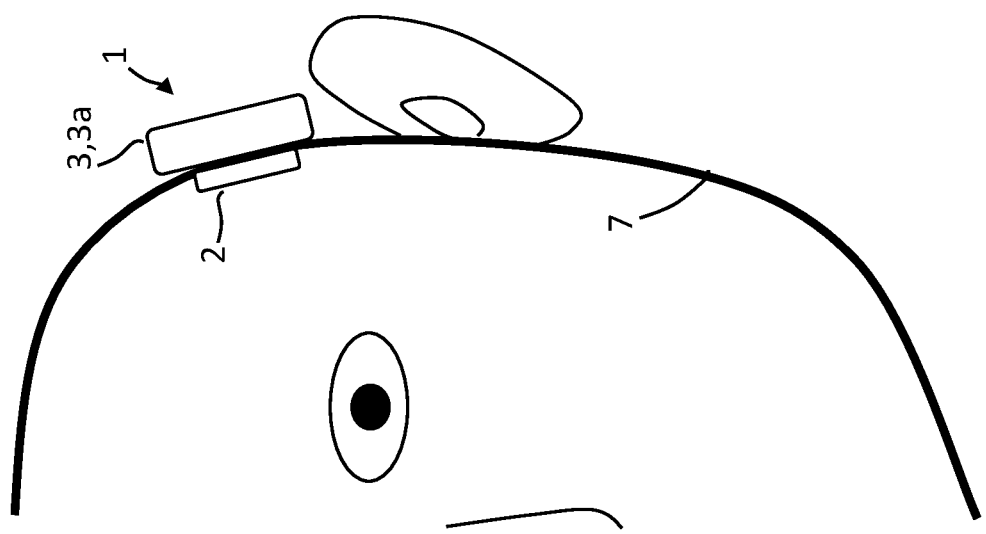

It is now referred to FIGS. 1A and 1B, which illustrate a hearing aid system 1 being worn by a user of the hearing aid system 1 arranged according to a conventional bone conducting system or a conventional cochlear implant system. In FIG. 1A, the implant unit 2 is coupled to the sound processor 3 via a magnet in the implant unit and the sound processor unit 3. In this example, the sound processor unit 3 may include one or more microphones for receiving an acoustical signal and convert it into an audio signal. In FIG. 1B. the hearing aid system 1 similar as described in FIG. 1A, however, in this example the sound processor unit 3 is connected to a Behind-the-ear unit 4 via a wired connection. The Behind-the-ear unit 4 may support the sound processor unit 3 in processing of the audio signal, or the Behind-the- Ear 4 unit may add more microphones to the hearing aid system 1 by, e.g. one or more microphones implemented into the Behind-the-Ear unit 4.

In FIGS. 2A and 2Bm an illustration of the sound processor 3 is seen. The sound processor comprises a housing 3a which has a first surface 6a facing towards a skin 7 of a user and at least a second surface 6b facing away from the skin 7 of the user. The housing 3a comprises an electrical circuitry 5 which is configured to receive and process an audio signal and to provide a processed audio signal. The housing 3a comprises a coil unit 8 configured to transfer the processed audio signal to the implant unit 2. In this example the coil unit 8 is arranged in vicinity to the first surface 6a of the housing 3a, The coil unit 8 is circumference a magnet 9, and where the magnet 9 is configured to align the sound processor unit 3 to the implant unit 2. The magnet 9 may be positioned in a magnet container comprised by the housing 3a. The housing comprises an antenna 10 including a radiating part 10a (not shown in this figure) configured to radiate an electromagnetic field for receiving the audio signal and/or a data signal. The antenna 10 includes an aperture 11 configured to receive the magnet 9. and wherein the antenna 10 is arranged between the coil unit 8 and the second surface 6b. In FIG. 2A, the aperture 11 is receiving at least a part of the magnet, and in FIG. 2B, the aperture 11 is receiving the complete magnet 9. In FIG. 2A, it is seen that the antenna 10 is bending such that a first part 10b of the antenna 10 is elevated from the first surface 6a with a first distance 12a which is less than a second distance 12b between a second part 10c of the antenna 10 and the first surface 6a. In FIG. 2B, the antenna 10 is seen as being flat having a constant distance to the first surface 6a. Alternatively, the antenna 10 may also be bended, as seen in FIG. 2A, while the complete magnet 9 is received by the aperture 11. In both FIGS. 3A and 3B, the magnet 9 includes a first end surface 17b arranged in vicinity to the second surface 6b of the housing 3a and a second end surface 17a arranged in vicinity to the first surface 6a of the housing 3a.

Figure 3B:
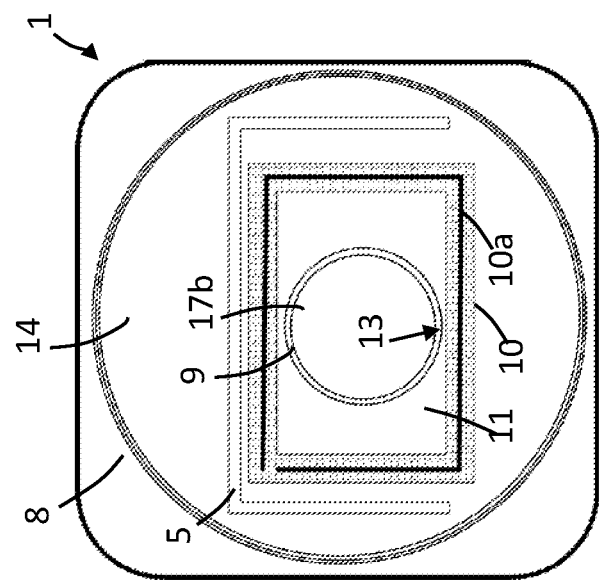
FIGS. 3A and 3B illustrate two examples of a hearing aid system where an antenna is circumference completely or partly a magnet.
Figure 3A:
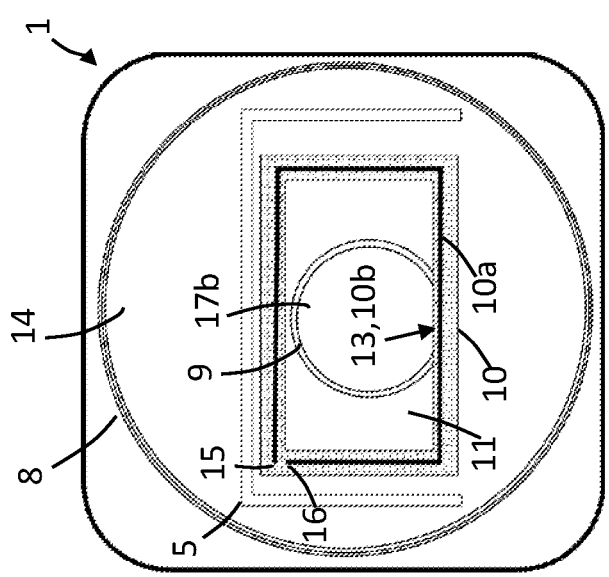

FIGS. 3A and 3B illustrate the coil unit 8 circumference the antenna 10, the electrical circuitry 5 and the magnet 9. Furthermore, the figures illustrate two example of antenna configurations, a first configuration where the a part of the antenna 10 is arranged between the magnet 9 and the second surface 6b of the housing 3a overlapping the magnet 9, see reference 13 FIG. 3A, and a second configuration where the complete antenna 10 is not arranged between the magnet 9 and the second surface 6b of the housing 3a, see reference 13 FIG. 3B. In FIG. 3A, the first part 10b of the radiating part 10a is arranged between the first end surface 17b and the second surface 6b of the housing 3a. In FIG. 3B, the antenna 10 is arranged such that the aperture 11 receives the complete magnet. In both figures, it is seen that the radiating part 10a is arranged circumferential to the aperture 11 having a first end 15 connected to a feeding point and a second end 16 connected to a ground plane.

FIGS. 4A and 4B illustrate the hearing aid system 1 with two different antenna configurations, where in both examples the coil unit 8 is connected to a decoupler 16 configured to decouple the coil unit 8 at an operating frequency of the antenna 10. The decoupler 16 may be an inductance or an integrated circuit having a resonance frequency at the operating frequency of the antenna 10.

FIGS. 5A to 5F illustrate different configurations of the antenna 10. In FIGS. 5A and 5B the antenna 10 includes another radiating part 20 which extends towards the first surface 6a of the housing 3a, and wherein the another radiating part 20 is connected to the radiating part 10a. In these examples, the another radiating part 20 is extending the electric length of the radiating part 10a, and the another radiating part 20 is contributing to the electric field being partly and/or fully parallel to the skin of the user generated by the radiating part 10a. In FIG. 5A, the another radiating part extends towards the first surface within the coil unit 8. In other words, the another radiating part 20 extends towards the first surface within an area 14 encircled by the coil unit 8. The another radiating part 20 extends towards the first surface 6a between the coil unit 8 and the magnet 9. In FIG. 5B, the another radiating part 20 extends towards the first surface 6a outside the coil unit 8. In other words, the another radiating part 20 extends towards the first surface 6a outside an area 14 encircled by the coil unit 8. The another radiating part 20 extends towards the first surface 6a between the coil unit 8 and the housing 3a.

In FIGS. 5C and 5D, the antenna 10 includes a passive resonant element 21 which in this example is connected capacitively or inductively to the radiating part 10a of the antenna 10, and where the passive resonant element 21 is arranged between the first surface 6a of the housing 3 and the radiating part 10a of the antenna 10. In FIG. 5C, the passive resonant element 21 extends towards the first surface within the coil unit 8. In other words, the passive resonant element 21 extends towards the first surface within an area 14 encircled by the coil unit 8. The passive resonant element 21 extends towards the first surface 6a between the coil unit 8 and the magnet 9. In FIG. 5B, the passive resonant element 21 extends towards the first surface 6a outside the coil unit 8. In other words, the passive resonant element 21 extends towards the first surface 6a outside an area 14 encircled by the coil unit 8. The passive resonant element 21 extends towards the first surface 6a between the coil unit 8 and the housing 3a.

In FIGS. 5E and 5F, the antenna includes a passive resonant element 21 which in these examples is connected galvanic via a connecting element 22 to the radiating part 10a. The connecting element 22 is arranged between the first surface 6a of the housing 3a and the radiating part 10a of the antenna 10. Furthermore, the passive resonant element 21 may be connected to a ground (not illustrated in this figure). In FIG. 5E, the connecting element 22 extends towards the first surface 6a of the housing 3a and within the area encircled 14 by the coil unit 8, and the passive resonant element 21 is arranged in parallel or partially in parallel with the first surface 6a of the housing 3a. The passive resonant element 21 may be arranged between the second end surface 17a of the magnet 9 and the first surface 6a of the housing 3a. In FIG. 5E, the connecting element 22 extends towards the first surface 6a of the housing 3a and outside the area 14 encircled by the coil unit 8, and the passive resonant element 21 is arranged in parallel or partially in parallel with the first surface 6a of the housing 3a. The passive resonant element 21 may be arranged between the second end surface 17a of the magnet 9 and the first surface 6a of the housing 3a, or the passive resonant element 21 may be arranged between the coil unit and the first surface 6a of the housing 3a.

In FIG. 6A, the antenna 10 is arranged such that the aperture 11 is configured to receive the magnet 9 if the user wants to remove or change the magnet 9 in the housing 3a. In this specific example, the antenna 10 is arranged between the second surface 6b and the coil unit 8. In FIG. 6B, the antenna 10 is arrange between an inner surface 31 and an outer surface 30 of the housing 3a.

The invention claimed is:

1. A sound processor unit configured as part of a hearing aid system also including an implant unit, wherein the sound processor unit comprises a housing including a first surface facing towards a skin of a user and at least a second surface facing away from the skin of the user, the housing comprising:
- an electrical circuitry configured to receive and process an audio signal and to provide a processed audio signal,
- a coil unit configured to transfer the processed audio signal to the implant unit,
- a magnet configured to align the sound processor unit to the implant unit, and
- an antenna including a radiating part configured to radiate an electromagnetic field for receiving the audio signal and/or a data signal, and wherein the antenna includes an aperture, wherein at least a part of the magnet is included inside an area bounded by the aperture, and
wherein the antenna is arranged between the coil unit and the second surface.

2. The sound processor unit according to claim 1, wherein the radiating part is arranged circumferential to the aperture having a first end connected to a feeding point and a second end connected to a ground plane.

3. The sound processor unit according to claim 1, wherein the coil unit is connected to a decoupler configured to decouple the coil unit at an operating frequency of the antenna.

4. The sound processor unit according to claim 3, wherein the decoupler is an inductance or an integrated circuit (IC) having a resonance frequency at the operating frequency of the antenna.

5. The sound processor unit according to claim 1, wherein an operating frequency of the antenna is within a frequency range of 2.4 GHz to 6 GHz, and an operating frequency of the coil unit is within a frequency range from 10 KHz to 150 KHz or about 60 KHz or about 120 KHz.

6. The sound processor unit according to claim 1, wherein the magnet includes a first end surface arranged in vicinity to the second surface of the housing and a second end surface arranged in vicinity to the first surface of the housing, and wherein a first part of the radiating part of the antenna is arranged between the first end surface and the second surface of the housing.

7. The sound processor unit according to claim 1, wherein the antenna is part of the electrical circuit.

8. The sound processor unit according to claim 1, wherein the antenna includes another radiating part extending towards the first surface of the housing, and wherein the another radiating part is connected to the radiating part.

9. The sound processor unit according to claim 8, wherein the another radiating part extending towards the first surface of the housing within or outside an area bounded by the coil unit.

10. The sound processor unit according to claim 1, wherein the antenna includes a passive resonant element being connected capacitively to the radiating part of the antenna, and wherein the passive resonant element is arranged between the first surface of the housing and the radiating part of the antenna.

11. The sound processor unit according to claim 1, wherein the antenna includes a passive resonant element being connected galvanic to the radiating part of the antenna via a connecting element, wherein the connecting element is arranged between the first surface of the housing and the radiating part of the antenna.

12. The sound processor unit according to claim 11, wherein the passive resonant element is connected to a ground.

13. The sound processor unit according to claim 12, wherein the passive resonant element is arranged within a near field of the electrical circuitry, and the passive resonant element being connected to a ground through energy dissolving means to terminate and dissolve electromagnetic radiation noise from at least at part of an area of the electrical circuit and/or other electrical components within the housing.

14. The sound processor unit according to claim 13, wherein the passive resonant element implements a notch filter filtering the electromagnetic radiation noise.

15. The sound processor unit according to claim 2, wherein the coil unit is connected to a decoupler configured to decouple the coil unit at an operating frequency of the antenna.

16. The sound processor unit according to claim 15, wherein the decoupler is an inductance or an integrated circuit (IC) having a resonance frequency at the operating frequency of the antenna.

17. The sound processor unit according to claim 2, wherein an operating frequency of the antenna is within a frequency range of 2.4 GHz to 6 GHz, and an operating frequency of the coil unit is within a frequency range from 10 KHz to 150 KHz or about 60 KHz or about 120 KHz.

18. The sound processor unit according to claim 2, wherein the magnet includes a first end surface arranged in vicinity to the second surface of the housing and a second end surface arranged in vicinity to the first surface of the housing, and wherein a first part of the radiating part of the antenna is arranged between the first end surface and the second surface of the housing.

19. The sound processor unit according to claim 2, wherein the antenna is part of the electrical circuit.

20. The sound processor unit according to claim 2, wherein the antenna includes another radiating part extending towards the first surface of the housing, and wherein the another radiating part is connected to the radiating part.

* * * * *